United States Patent
Niedospial, Jr.

(10) Patent No.: US 6,666,852 B2
(45) Date of Patent: Dec. 23, 2003

(54) AXIALLY ACTIVATED VIAL ACCESS ADAPTER

(75) Inventor: John J. Niedospial, Jr., Burlington, NJ (US)

(73) Assignee: Bracco Diagnostics, Inc., Princeton, NJ (US)

(*) Notice: Subject to any disclaimer, the term of this patent is extended or adjusted under 35 U.S.C. 154(b) by 366 days.

(21) Appl. No.: 09/728,984

(22) Filed: Dec. 4, 2000

(65) Prior Publication Data

US 2002/0066715 A1 Jun. 6, 2002

(51) Int. Cl.[7] .................................................. A61M 5/32
(52) U.S. Cl. ............................ 604/415; 604/414; 604/88
(58) Field of Search ................................. 604/403, 411, 604/415, 88, 414; 215/247

(56) References Cited

U.S. PATENT DOCUMENTS

| | | | |
|---|---|---|---|
| 2,326,490 A | 8/1943 | Perelson | 215/47 |
| 2,342,215 A | 2/1944 | Perelson | 215/38 |
| 2,667,986 A | 2/1954 | Perelson | 215/48 |
| 3,872,992 A | 3/1975 | Larson | 215/249 |
| 3,940,003 A | 2/1976 | Larson | 215/247 |
| 3,977,555 A | 8/1976 | Larson | 215/247 |
| 4,412,623 A | 11/1983 | Schmidt | 215/11 |
| 5,232,109 A | 8/1993 | Tirrell et al. | 215/247 |
| 5,364,386 A | 11/1994 | Fukuoka et al. | 215/411 |
| 5,379,907 A * | 1/1995 | Niedospial et al. | 215/247 |
| 5,429,256 A | 7/1995 | Kestenbaum | 215/247 |
| 5,433,330 A | 7/1995 | Yatsko et al. | 215/247 |
| 5,620,434 A | 4/1997 | Brony | |
| 5,921,419 A * | 7/1999 | Niedospial et al. | 215/247 |
| 5,924,584 A * | 7/1999 | Hellstrom et al. | 215/247 |
| 5,971,181 A * | 10/1999 | Niedospial et al. | 215/247 |
| 6,090,092 A * | 7/2000 | Fowles et al. | 604/413 |
| 6,287,289 B1 * | 9/2001 | Niedospial, Jr. | 206/828 |

FOREIGN PATENT DOCUMENTS

| | | |
|---|---|---|
| DE | 29708202 | 8/1997 |
| EP | 0205345 | 12/1986 |
| EP | 0450096 | 10/1991 |
| GB | 856544 | 12/1960 |
| WO | WO 98/37855 | 9/1998 |

* cited by examiner

Primary Examiner—Angela D. Sykes
Assistant Examiner—Leslie R. Deak
(74) Attorney, Agent, or Firm—M. Caragh Noone; Bryan M. Peckjian

(57) ABSTRACT

Axially activated vial access adapter allowing repeated withdrawal of a medical fluid contained in the container by the use of a needleless device such as a syringe barrel or IV set having a luer connector. The axially activated vial access adapter includes: an elastomeric stopper having a cavity extending from its distal end to its proximal end; a bottom insert positioned in the cavity of the elastomeric stopper; and a top insert of tube-like configuration slideably positioned in the bottom insert. The top insert contains a plug on its proximal end, and a male luer connector on its distal end for attachment to a syringe barrel or an IV set having a female luer connector. Moving the top insert distally or proximally, the plug on the proximal end of the top insert opens or closes the cavity in the elastomeric stopper thereby opening or closing fluid communication between the medical fluid contained in the container and the syringe barrel or IV set having a luer connector.

20 Claims, 3 Drawing Sheets

AXIALLY ACTIVATED VIAL ACCESS ADAPTER

FIELD OF THE INVENTION

The present invention is directed to an axially activated vial access adapter used in association with a container, such as a bottle or vial, for the containment and delivery of parenteral solutions, such as diagnostic contrast media and drug formulations. More particularly, the invention relates to a needleless access means having an axially activated seal therein for opening and closing the container for delivery of the parenteral solution to a site through luer connections.

BACKGROUND OF THE INVENTION

There is an increasing worldwide demand for medical safety devices including safety syringes and other transfer devices. Needle stick injuries number about one million per year in the U.S. alone, resulting in thousands of hepatitis C infections.

Devices have been developed in an effort to prevent accidental needle strike injuries to practitioners and patients. Such injuries are known to spread infectious diseases including hepatitis and AIDS. One of the main features of these devices is the lack of exposed sharp needles. The closures or stoppers have built-in access means to the content of the containers, such as vials, cartridges and bottles. The closures or stoppers in these devices serve the dual function of hermetically sealing the container while allowing safe access to the content therethrough.

Stopper systems for containers such as vials and bottles are made of materials that are resistant to chemicals and pharmaceuticals such as corrosive materials, reagents, parenteral solutions and solid formulations reconstitutable with a solvent prior to use. The most commonly used stopper/container system for such products has been glass or plastic bottles and vials equipped with stoppers made of elastomeric materials. The system provides for good hermetical seal, safe storage and easy access to the content through the elastomeric stopper via the use of an infusion spike or a syringe when withdrawal of the content is desired. The elastomeric stopper used generally comprises an elastomeric base, such as natural or synthetic rubber and an inert coating covering at least some portions of the stopper. The coating used includes chlorobutyl rubber, polymeric fluorocarbon resins such as polytetrafluoroethylene and various thermoplastic films. The coating is intended to insulate the elastomeric stopper base from the contents of the container in order to prevent contact and possible chemical reactions therebetween.

Generally, the elastomeric stopper is of cylindrical shape and has a flange head portion overlying the open top end of the container. Integral with the head portion is a body portion which extends into the open end and seated in the neck portion of the container, the diameter of the body portion being somewhat larger than the inside diameter of the container so that a tight seal is created between the body portion and the wall of the container. The lower end of the body portion is beveled towards the central, longitudinal axis of the body portion to facilitate the insertion of the body portion into the container. The circular bottom surface that faces the contents of the container is substantially planar and is imperforate, having no recess therein. The head portion of the stopper is provided with a central recess extending downwardly from the top thereof a substantial distance into the body portion so that the central recess and the circular bottom surface define a diaphragm. The walls forming the recess are generally cylindrical but may be provided with one or more circular protuberances extending inwardly to terminate just short of the center line of the stopper. The circular protuberances serve to press against and hold the needle of a syringe when the needle is inserted through the recess to penetrate the diaphragm for removal of the contents of the container. The elastomeric stopper is held in position by a metal ring or cap usually constructed of aluminum. The metal ring or cap has a removable center opening for allowing insertion of the syringe needle into the container.

Various stopper and access systems exist in the prior art to hold and remove the contents of containers. For example, a rubber stopper for use in vials may comprise an outer wall which serves as a seal between the vial and the stopper and an inner wall forming a chamber in the center of the stopper, the bottom portion of the inner wall serving as a diaphragm. A hollow needle, having a sharp end for piercing the diaphragm, and an outer end exposed for connection with a syringe may be carried by the outer wall. A syringe connected to the outer end of the needle and pushed inwardly effects piercing of the diaphragm thereby permitting aspiration of the contents of the vial.

Similarly, a stopper body may have a hollow needle therein where one end of said hollow needle is in constant communication with the contents of the vial, and the other end is sealed by a penetrable, thin membrane. When withdrawal of the contents of the vial is desired, a syringe is inserted into the stopper to penetrate the thin membrane and to engage the other end of the hollow needle. When the syringe is removed, the thin membrane self-closes to maintain the hollow needle and the contents of the vial sterile.

Additionally, attempts to prevent accidental needle strikes have included a needleless access stopper used on containers with a cannula having a blunt, stopper penetrating tip; a closure assembly having an elastomeric membrane capable of being ruptured by a luer connector; and an elastomeric stopper for a bottle which includes an annular protuberance which forms a second seal with the shaft of a spike inserted in the stopper to prevent leakage, blow-out and introduction of particulate matter into the fluid-containing bottle.

Another attempt includes an infusion unit which comprises a flexible, large container, a small medicine vial and a pipe which serves to communicate between the large, flexible container and the small medicine vial. The large container is adapted to hold a solvent or diluent, while the medicine vial contains a powdery medicine which is to be mixed and dissolved in the solvent or diluent contained in the large, flexible container. Upon dissolution, the mixed medicine is discharged through an outlet at the lower end of the large container for infusion into a patient.

Alternatively, the prior art discloses a drug withdrawal system for a vial which comprises: a vial containing a medicament therein and closed with a rubber gasket; and an apparatus which snap fits on top of the vial. The apparatus comprises: a chassis and a cap which is attached to the cap by a living hinge. The chassis is cylindrical and has vertical grooves on the external sides to facilitate handling. The top of the chassis has a central opening. The chassis includes a male luer lock adapter having external threads thereon, and a ferrule structure the lower end of which has a hollow sharpened lance. The apparatus is used with a syringe having a female luer lock connector which snap fits with the male luer lock adapter.

In use, the cap cover is opened, and a syringe is screwed onto the outer end of the adapter. The syringe is then tightened on the adapter which moves the lance downward and the lance penetrates the gasket on the vial thereby establishing flow communication with the content of the vial. The content of the vial is withdrawn by pulling back on the plunger of the syringe. The syringe is then removed with the content therein ready to receive a needle assembly for injecting the content into a patient.

The prior art also discloses a multiple use universal stopper having an M-shaped elastomeric membrane capable of being ruptured by a luer connector, wherein the M-shaped elastomeric membrane reseals itself after being punctured by the luer connector.

The present invention provides sealing and access means for containers, such as bottles or vials made of glass or plastic containing medical fluids, such as x-ray contrast media and parenteral liquids. The access means provides for hermatic sealing, safe handling, sterilization and storing. The sealing means are designed for multiple use so that the medical fluid can be accessed repeatedly. Specifically, the invention relates to a needleless access means having an axially activated seal therein for opening and closing the container for delivery of a parenteral solution to a site through a luer connector. After each withdrawal of the desired amount of the medical fluid, the access means is closed thereby preventing contamination of the medical fluid by air-born particles, such as dust and bacteria.

SUMMARY OF THE INVENTION

In accordance with one aspect of the present invention, an axially activated vial access adapter is provided to allow repeated access to a medical fluid, such as diagnostic, therapeutic or animal healthcare formulation, contained in a container, such as a vial, by the use of any external device that is equipped with a luer connector, such as syringe or cartridge barrels and IV sets.

In another aspect, the present invention provides a method for repeatedly accessing a medical fluid contained in a container equipped with the axially activated vial access adapter and closing the container after each use in order to prevent contamination of the medical fluid by air-born particles in the environment, such as dust and bacteria. The axially activated vial access adapter contains no "sharps", such as sharp or blunt needle cannulas or spikes and, therefore, the use thereof does not carry the risk of accidental injuries and transmittance of contagious diseases.

The axially activated vial access adapter contains three main components:
  a) an elastomeric stopper having a cylindrical cavity in the center portion thereof;
  b) a cylindrical bottom insert having a cylindrical cavity therein positioned in the cylindrical cavity of the elastomeric stopper; and
  c) a cylindrical top insert of tube-like configuration having a plug portion positioned in the cylindrical cavity of the cylindrical bottom insert.

The container for accommodating the present invention is made of glass or a polymeric material known in the art. When the container is made of glass it is in the shape of a vial or bottle. Plastic containers may be in the shape of a vial, bottle or bag. The vial or bottle is of rigid or semi-flexible polymeric material, while the bag is of a pliable polymeric material. In all the configurations the container is provided with a neck portion which is sufficiently rigid and is capable of retaining its dimensions when the axially activated vial access adapter is inserted thereinto. The container has a neck portion terminating in an open end with a rigid or semi-rigid exit port to receive the axially activated vial access adapter which is inserted into the access port to seal the content therein and to maintain it in sterile condition.

The elastomeric component of the present invention is of cylindrical configuration, having a horizontal top surface, a horizontal bottom surface, an outside wall, and an inside wall. The elastomeric stopper comprises: a head portion, and a skirt portion. The head portion comprises a flange extending laterally outwardly from the outside wall and is designed to cover the transverse and surface of a vial. The inside wall defines an opening within the head and skirt portions to provide a cylindrical chamber or cavity for holding the cylindrical bottom insert. The skirt portion is recessed so that the cylindrical bottom insert becomes embedded in the cylindrical chamber or cavity when the cylindrical bottom insert is inserted into the cylindrical chamber or cavity. The center of the horizontal bottom surface of the elastomeric stopper is provided with a small opening to receive the plug portion of the cylindrical top insert.

The elastomeric stopper is made of an elastomeric base, such as a natural or synthetic rubber preferably having an inert, polymeric coating thereon covering at least the medical fluid contacting portions of the stopper. Examples of elastomeric materials from which the stopper can be made include butyl rubber, isoprene rubber, silicone rubber, halogenated rubber and ethylene propylene therpolymer. Specific examples of a synthetic elastomeric rubber include: the $CH_2CF_2$—$C_3F_6(C_3F_5H)$ and the $C_2F_4$—$C_2F_3OCF_3$ series of elastomers made by DuPont under the tradenames of VITON® and CARLEZ®; the fluoro-silicon rubbers, such as made by Dow Coming under the tradename of SILASTIC®; and polyisobutylenes, such as VISTANEX MML-100 and MML-140; and halogenated butyl rubber, such as CHLOROBUTYL 1066 made by Exxon Chemical Company. These and other suitable elastomers may be made into the desired stopper configuration by known methods. Such methods typically include the use of a curing agent, a stabilizer and, a filler and comprise a primary and a secondary curing step at elevated temperatures. The coating covering the elastomeric stopper may be of chlorobutyl rubber, polymeric fluorocarbon resins and thermoplastic films. Preferably, the elastomeric stopper is made of thermoplastic elastomers which include thermoplastic polymethanes, styrenic block copolymers, copolyesters, rubber olefin alloys, neoprene, urea-formaldehyde, polyvinyl formaldehyde, phenolformaldehyde resins, and polystyrenes.

The cylindrical bottom insert component of the present invention is positioned in the elastomeric stopper and is designed to receive the top inset component of the present invention. Together the bottom and top inserts function as an axially activable valve which can be opened or closed by moving the top insert in the distal or proximal directions with respect to the bottom insert.

The cylindrical bottom insert comprises:
  a first wall; and
  a second wall spaced from the first wall towards the center of the cylindrical bottom insert and extends parallel to the first wall; each of the walls having a proximal end and a distal end. The proximal ends of the first and second walls are connected by a horizontal bottom wall forming a concentric double-walled cylinder closed at the proximal end. The height of the second wall is less than the height of the first wall. First and second walls and horizontal bottom wall are integral with each other and are preferably made by injection molding. Both first and second walls terminate in a rim at their distal ends, the rims projecting inwardly towards the center of the bottom insert. Additionally, the first wall contains an inwardly projecting protuberance spaced from the rim towards the horizontal bottom wall. Said rim and said protuberance on the first wall limits the up and down movement of the cylindrical top insert from the open to the closed position.

The rim on the second wall serves to slideably engage a portion of the cylindrical top insert which comprises:
an elongated tubular body having a top portion and a bottom portion;
a skirt portion surrounding the bottom portion of the elongated tubular body and is spaced therefrom, leaving a cylindrical gap therebetween.

The elongated tubular body comprises:
a rim on its distal end projecting towards the inside wall of the elastomeric stopper and serving as a male luer connector to mate with an external female luer connector; and
a plug on the proximal end serving to close the small opening in the bottom surface of the elastomeric stopper.

The skirt portion of the top insert comprises:
a cylindrical side wall having an outside surface, an inside surface, a distal end and a proximal end; and
a horizontal wall at the distal end of the skirt portion connecting the cylindrical wall to the tubular body of the top insert, wherein: the horizontal wall terminates in a rim portion projecting away from the cylindrical side wall and is designed to slideably move between the rim on the first wall of the bottom insert and just below the protuberance on the first wall of the bottom insert when the top insert travels from the open position to the closed position; and the proximal end of the skirt portion is provided with a rim and a protuberance projecting towards the elongated tubular body and frictionally press against the second wall of the bottom insert when the top insert is moved from the open to the closed position.

It is to be noted that when the top insert is in the closed position: the plug in the tubular body of the top insert seals the small opening in the bottom surface of the elastomeric stopper; the horizontal wall on the top portion of the skirt reaches the rim on the second wall of the bottom inset; and the rim on the horizontal wall of the skirt portion passes the protuberance on the inside of the first wall in the bottom insert.

In another aspect, the present invention provides a method for repeatedly accessing a medical fluid contained in a container equipped with the axially activated vial access adapter. The method comprises the steps of:
a) providing the axially activated vial access adapter as described herein and placing it on the exit port of a container containing a medical fluid therein;
b) attaching an external access means having a female luer connector to the male luer connector in the axially activated vial access adapter;
c) exerting a pulling force on the external access means to move the top insert into the open position;
d) delivering a desired amount of the medical fluid to a patient;
e) exerting a pushing force on the external access means to move the top insert into the closed position and
f) removing the external access means from the axially activated vial access adapter.

The external access means includes a syringe barrel equipped with a female luer connector and an IV set equipped with a female luer connector.

The bottom and top insert components of the axially activated vial access adapter is made of thermoplastic materials such as polyethylene, polypropylene, polystyrene, polycarbonate, polymethylpentene, cyclic olefin polymers, acrylic polymers, methacrylic polymers, and acrylonitrile-butadiene styrene.

DETAILED DESCRIPTION OF THE INVENTION

Figure 1:
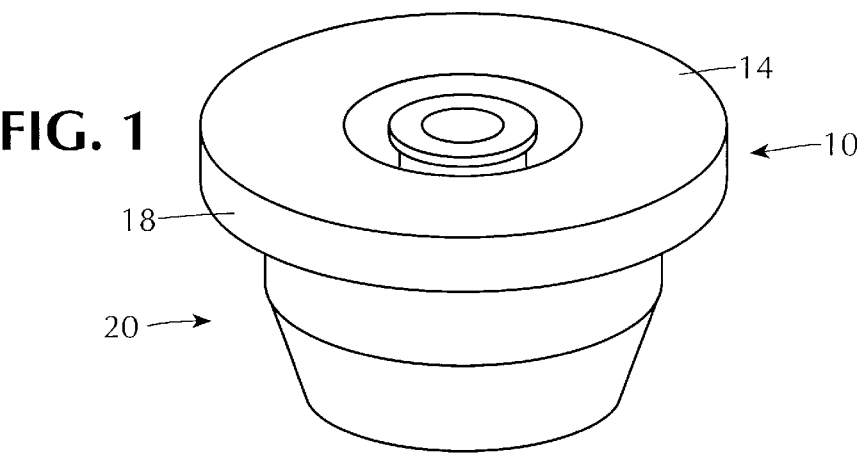
FIG. 1 is a perspective view of the axially activated vial access adapter of the present invention.
Figure 2:
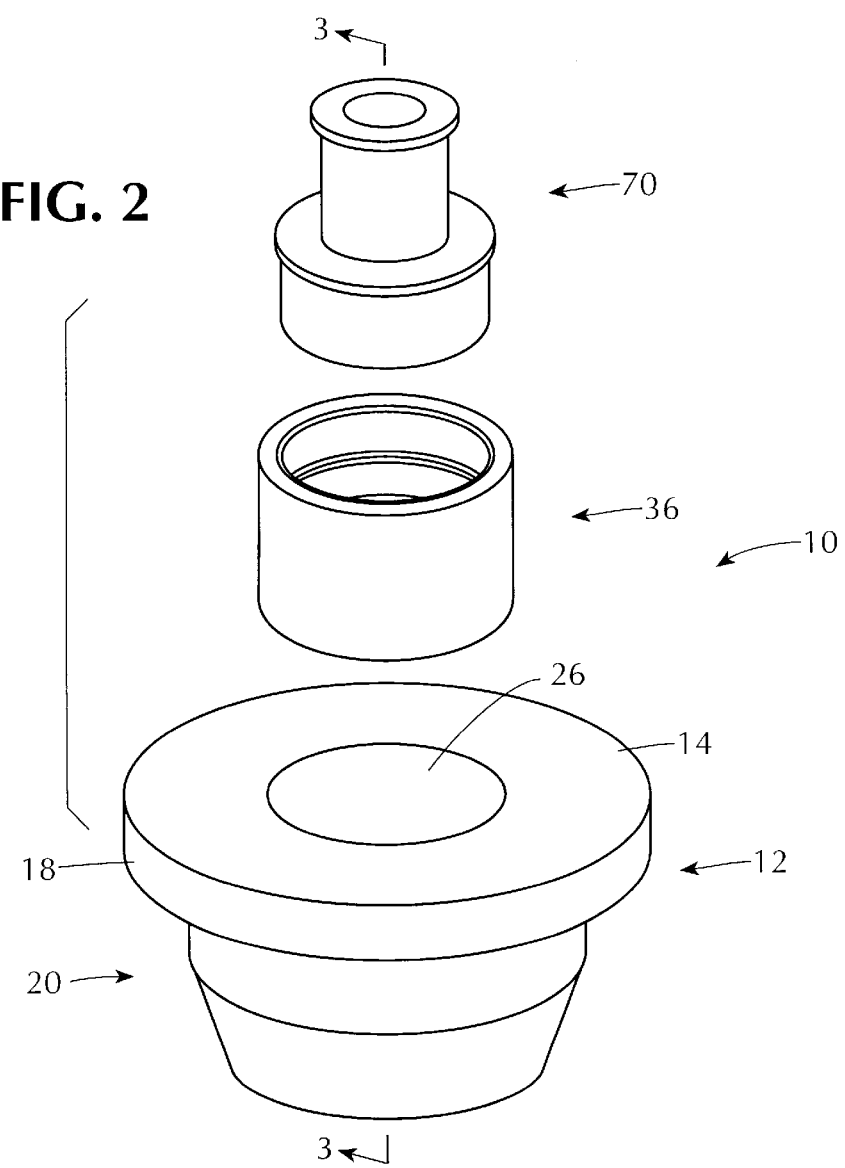
FIG. 2 is an exploded view thereof showing the three components constituting the invention.
Figure 3:
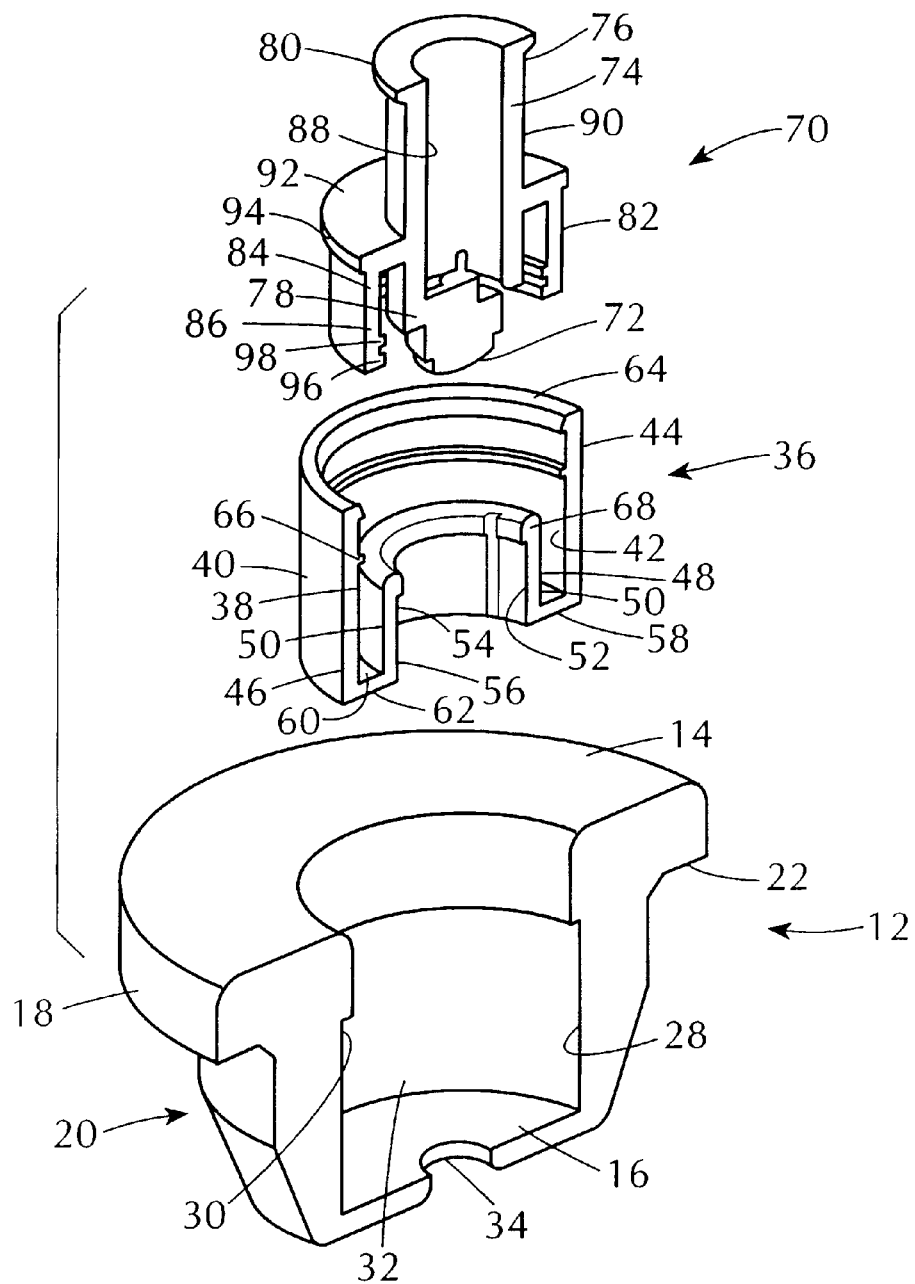
FIG. 3 is a cross-sectional view of the three components taken along the line 3—3 of FIG. 2.

The present invention provides repeated access to a medical fluid contained in a vial by the use of an external access means equipped with a luer connector. The method of accessing the medical fluid includes the steps of: placing the axially activated vial access adapter on the exit port of the vial containing the medical fluid therein; attaching the external access means to the axially activated vial access adapter; exerting a pulling force on the external access means to move the top insert into the open position; delivering a desired amount of the medical fluid to a site; exerting a pushing force on the external access means to move the top inset into the closed position; and removing the external access means form the activated vial access adapter. This process can be repeated until the content of the vial is exhausted.

Reference is now made to the drawings of FIGS. 1–5 illustrating the present invention.

The axially activated vial access adapter, generally designated by the numeral 10, comprises three component parts:
an elastomeric stopper, generally designated by the numeral 12;
a cylindrical bottom insert, generally designated by the numeral 36, positioned in the elastomeric stopper; and
a cylindrical top insert, generally designated by the numeral 70, positioned in the bottom insert.

The elastomeric stopper 12 having a top surface 14 and a bottom surface 16 comprises: a head potion 18 and a skirt portion 20. The head portion comprises a flange 22 extending laterally outwardly from skirt potion 20 and is designed to cover the transverse end surface of a vial. A cylindrical inside wall 24 defines an opening 26 in the head portion 18, while a cylindrical inside wall 28 defines an opening in the skirt portion 20 of the elastomeric stopper, said openings being contiguous with each other. Cylindrical inside wall 28 in the skirt portion contains recess 30 providing space for the bottom insert 36. The bottom surface 16 of the elastomeric stopper 12, and the cylindrical inside wall 28 containing recess 30 therein, define a cylindrical chamber 32 for housing and securely holding bottom insert 36. In the center of bottom surface 16 of the elastomeric stopper 12 a small opening 34 is provided to receive the plug portion 72 of the cylindrical top insert 70.

The cylindrical bottom insert, generally designated by the numeral 36 is positioned in the elastomeric stopper 12 comprising:

a first wall 38 having an outside surface 40, an inside surface 42, a top portion 44, and a bottom portion 46;

a second wall 48 having an outside surface 50, an inside surface 52, a top portion 54, and a bottom portion 56.

The second wall is spaced from the first wall toward the center of cylindrical bottom insert and is connected to the first wall by a horizontal wall 58 having a top surface 60 and a bottom surface 62. The height of the second wall is less than the height of the first wall and, preferably, is about half thereof Preferably, the first wall, the second wall and the horizontal bottom wall are integral with each other and are made by injection molding.

First wall 38 has a rim 64 on its top portion 44 and a protuberance 66, both the rim and the protuberance projecting toward the second wall 48 and serving as knobs to stop the sliding movement of the top insert 70 between the open and closed positions. Protuberance 66 is at about ⅔ of the height of the first wall from the horizontal wall 58.

Second wall 48 at its top portion 54 also has a rim 68 projecting towards the center of the axially activated vial access adapter 10 and serves to slideably engage a portion of the cylindrical top insert 70.

Cylindrical bottom insert 36 is positioned into elastomeric stopper 12 by a snap-on motion as follows. Cylindrical bottom insert is held in a rightside-up orientation and pushed through the opening 26 in head portion of elastomeric stopper. The cylindrical bottom insert rubs against the inside wall 24 of the head portion. While the cylindrical bottom portion is slightly larger in the transverse direction than the opening in the elastomeric stopper, it fits through the opening easily since the elastomeric stopper is flexible and resilient. After passing through the opening in the head portion, the cylindrical bottom portion reached recess 30, which forms chamber 32 in the skirt portion 20, and snaps thereinto. The chamber will hold the cylindrical bottom insert securely without allowing for axial or transverse movements.

Cylindrical top insert 70, positioned into cylindrical bottom insert 36, comprises:

an elongated tubular body 74 having a top portion 76, a bottom portion 78, wherein the top portion terminates in a rim 80 and the bottom portion terminates in a plug 72;

a skirt portion 82 spaced proximally from the rim surrounding the bottom of the elongated tube having a top portion 84 and a bottom portion 86, an inside wall 88, and outside wall 90, wherein: the top portion is closed by a horizontal wall 92 having a rim 94 thereon extending outwardly from the outside wall 90; and the bottom portion is provided with a rim 96 and a protuberance 98 spaced distally from rim 96, both rim and protuberance extending towards elongated tube 74.

Figure 4:
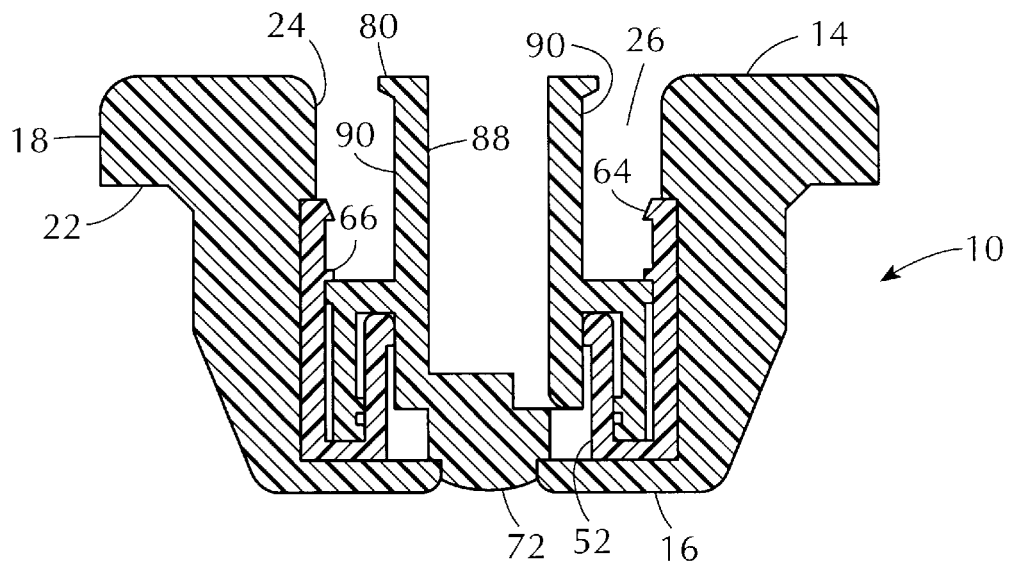
FIG. 4 is a cross-sectional view of the axially activated vial access adapter in the closed position.
Figure 5:
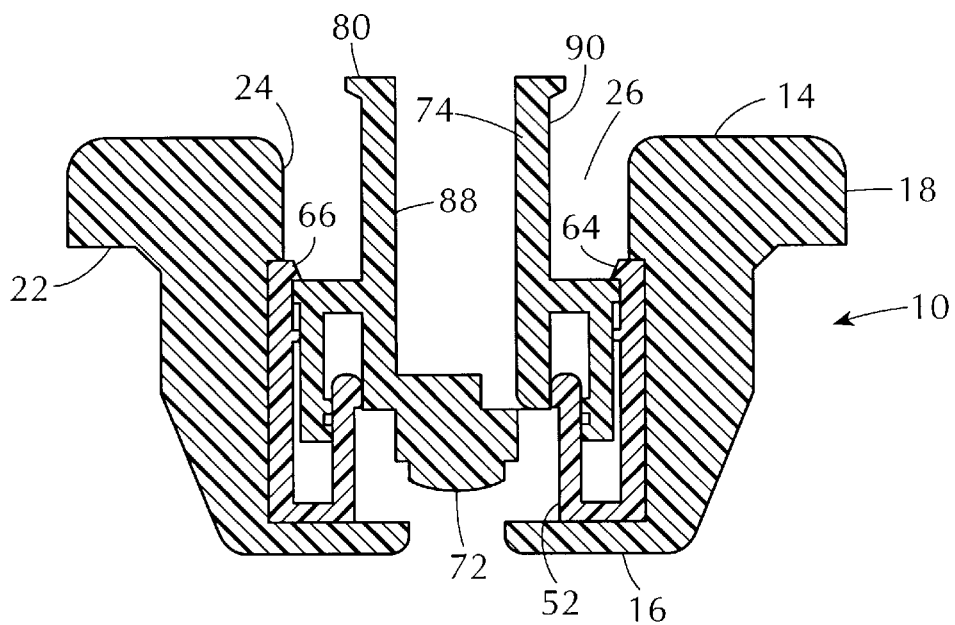
FIG. 5 is a cross-sectional view of the axially activated vial access adapter in the open position.

Cylindrical top insert 70 is positioned in cylindrical bottom insert as shown in FIGS. 4 and 5.

As shown and described, the present invention provides a safe and repeated access to a medical fluid contained in a container without the danger of injuries caused by needles or spikes.

Other advantages of the invention include the following: safe handling when used as packaging for nuclear drug products where a spill may cause an environmental hazard; less exposure to the medical practitioner by providing quicker access to nuclear drug products contained in the container; provides for multi-dosing of drug products transferred to smaller containers or delivered to several patients; it is autoclavable; and it is inexpensive to manufacture, i.e. the elastomeric stopper and the bottom insert can be two-shot molded.

| PARTS LIST | |
|---|---|
| Axially activated vial access adapter, generally designated | 10 |
| Elastomeric stopper, generaly designated | 12 |
| Top surface of elastomeric stopper | 14 |
| Bottom surface of elastomeric stopper | 16 |
| Head portion of elastomeric stopper | 18 |
| Skirt portion of elastomeric stopper, generally designated | 20 |
| Flange on head portion of elastomeric stopper | 22 |
| Cylindrical inside wall in head portion | 24 |
| Opening in head portion | 26 |
| Cylindrical inside wall in skirt portion | 28 |
| Recess in skirt portion | 30 |
| Cylindrical chamber in skirt portion | 32 |
| Small opening in bottom surface of elastomeric stopper | 34 |
| Cylindrical bottom insert, generally disignated | 36 |
| First wall of bottom insert | 38 |
| Outside surface of first wall | 40 |
| Inside surface of first wall | 42 |
| Top portion of first wall | 44 |
| Bottom portion of first wall | 46 |
| Second wall of bottom insert | 48 |
| Outside surface of second wall | 50 |
| Inside surface of second wall | 52 |
| Top porion of second wall | 54 |
| Bottom portion of second wall | 56 |
| Horizontal wall connecting first and second walls | 58 |
| Top surface of horizontal wall | 60 |
| Bottom surface of horizontal wall | 62 |
| Rim on first wall | 64 |
| Protuberance on first wall | 66 |
| Rim on second wall | 68 |
| Cylindrical top insert, generally designated | 70 |
| Plug of the cylindrical top insert | 72 |
| Elongated tubular body of cylindrical top insert | 74 |
| Top portion of elongated tubular body | 76 |
| Bottom portion of elongated tubular body | 78 |
| Rim of elongated tubular body | 80 |
| Skirt portion of cylindrical top insert | 82 |
| Top portion of skirt portion | 84 |
| Bottom portion of skirt portion | 86 |
| Inside wall of top insert | 88 |
| Outside wall of top insert | 90 |
| Horizontal wall on top portion | 92 |
| Rim on top portion of horizontal wall | 94 |
| Rim on bottom portion of horizontal wall | 96 |
| Protuberance on bottom portion of horizontal wall | 98 |

Having described the invention, it will be apparent to those skilled in the art that various changes and modifications may be made thereto limited only by the scope of the appended claims.

What is claimed is:

1. An axially activated vial access adapter for allowing repeated access to a medical fluid contained in a container by the use of an external device equipped with a luer connector, said axially activated vial access adapter comprising:

a) an elastomeric stopper for sealing a container, said container containing a medical fluid therein, said elastomeric stopper having a distal end and a proximal end and a cylindrical cavity in its center portion having an inside wall therein extending from said distal end to said proximal end;

b) an axially activateable valve positioned in said cylindrical cavity of said elastomeric stopper comprising a cylindrical bottom insert and a cylindrical top insert, said cylindrical bottom insert having a cylindrical cavity, said cylindrical top insert having a distal end and a proximal end for slideably engaging said cylindrical bottom portion;

c) the cylindrical top insert being of tube-like configuration wherein said distal end terminates in a rim serving as a male luer connector for attachment to an external female luer connector and said proximal end terminates in a plug; and wherein:

said axially activated vial access adapter is in a closed position when an external force is exerted on the cylindrical top insert in a proximal direction by which said plug closes the proximal end of said elastomeric stopper, and said axially activated vial access adapter is in a open position when an external force is exerted on the cylindrical top insert in a distal direction by which said plug opens the proximal end of said elastomeric stopper thereby allowing withdrawal of a medical fluid contained in said container.

2. The axially activated vial access adapter of claim 1 wherein said container is a vial, bottle, or a bag equipped with a rigid or semi-rigid exit port to receive said axially activated vial access adapter.

3. The axially activated vial access adapter of claim 2 wherein said vial and said bottle are made of glass or a polymeric material.

4. The axially activated vial access adapter of claim 1 wherein said medical fluid is a diagnostic medium.

5. The axially activated vial access adapter of claim 1 wherein said elastomeric stopper is made of natural or synthetic rubber.

6. The axially activated vial access adapter of claim 5 wherein said elastomeric stopper is made of butyl rubber, isoprene rubber, silicone rubber, halogenated rubber or ethylene propylene therpolymer.

7. The axially activated vial access adapter of claim 5 wherein said elastomeric stopper is coated with chlorobutyl rubber, polymeric fluorocarbon resins or thermoplastic films.

8. The axially activated vial access adapter of claim 1 wherein said top insert and said bottom insert are made of a thermoplastic material.

9. The axially activated vial access adapter of claim 8 wherein said thermoplastic material is selected from the group consisting of polyethylene, polypropylene, polystyrene, polycarbonate, polymethylpentene, cyclic olefin polymers, acrylic polymers and methacrylic polymers.

10. A method of accessing a medical fluid contained in a container equipped with an axially activated vial access adapter comprising the steps of:

1) providing an axially activated vial access adapter comprising:
   a) an elastomeric stopper for sealing a container, said elastomeric stopper having a distal end and a proximal end and a cylindrical cavity in its center portion having an inside wall therein extending from said distal end to said proximal end;
   b) an axially activateable valve positioned in said cylindrical cavity of said elastomeric stopper comprising a cylindrical bottom insert and a cylindrical top insert, said cylindrical bottom insert having a cylindrical cavity, said cylindrical top insert having a distal end and a proximal end for slideably engaging said cylindrical bottom portion;

the cylindrical top insert being of tube-like configuration wherein said distal end and a proximal end slideably positioned in the cylindrical cavity of said bottom portion insert, wherein said distal end terminates in a rim serving as a male luer connector for attachment to an access means and said proximal end terminates in a plug adapted to open and close the proximal end of said elastomeric stopper; and wherein said axially activated vial access adapter is in a closed position when an external force is exerted on the cylindrical top insert in a proximal direction by which said plug closes the proximal end of said elastomeric stopper, and said axially activated vial access adapter is in a open position when an external force is exerted on the cylindrical top insert in a distal direction by which said plug opens the proximal end of said elastomeric stopper thereby allowing withdrawal of a medical fluid contained in said container;

2) placing said axially activated vial access adapter on the exit port of a container containing medical fluid therein;

3) attaching an external access means having a female luer connector to said male luer connector of the cylindrical top insert;

4) exerting an external force in a distal direction on said cylindrical top insert to move said cylindrical top insert into an open position thereby opening a flow channel and establishing fluid communication between said medical fluid contained in the container and the external luer connector; and 5) delivering said medical fluid or a portion thereof to a patient.

11. The method of claim 10 wherein said external access means is a syringe barrel equipped with a female luer connector.

12. The method of claim 10 wherein said external access means is an IV set equipped with a female luer connector.

13. The method or claim 10 wherein said container is a vial, bottle, or a bag equipped with a rigid or semi-rigid exit port to receive said axially activated vial access adapter.

14. The method of claim 13 wherein said vial or said bottle is made of glass or a polymeric material.

15. The method of claim 10 wherein said medical fluid is a diagnostic medium, a thermoplastic formulation, or an animal health care formulation.

16. The method of claim 10 wherein said elastomeric stopper is made of natural or synthetic rubber or a thermoplastic elastomer.

17. The method of claim 16 wherein said elastomeric stopper is made of butyl rubber, isoprene rubber, silicone rubber, halogenated rubber or ethylene propylene therpolymer, thermoplastic polymethanes, styrene block copolymers, copolyesters, rubber olefin alloys, neoprene, urea formaldehyde, polyvinyl formaldehyde, phenolformaldehyde resins and polystyrenes.

18. The method of claim 10 wherein said elastomeric stopper is coated with chlorobutyl rubber, polymeric fluorocarbon resins or thermoplastic films.

19. The method of claim 10 wherein said top insert and said bottom insert are made of a thermoplastic material.

20. The method of claim 19 wherein said thermoplastic material is selected from the group consisting of polyethylene, polypropylene, polystyrene, polycarbonate, polymethylpentene, cyclic olefin polymers, acrylic polymers, methacrylic polymers, and acrylonitrile-butadiene styrene.

* * * * *